US011140957B2

(12) United States Patent
Park et al.

(10) Patent No.: US 11,140,957 B2
(45) Date of Patent: Oct. 12, 2021

(54) PROTECTIVE CRADLE AND MODULAR POUCHES

(71) Applicant: KONINKLIJKE PHILIPS N.V., Eindhoven (NL)

(72) Inventors: Jae Park, Medford, MA (US); Stephen Robert Heath, Andover, MA (US); Min Zhao, Acton, MA (US)

(73) Assignee: Koninklijke Philips N.V., Eindhoven (NL)

( * ) Notice: Subject to any disclaimer, the term of this patent is extended or adjusted under 35 U.S.C. 154(b) by 232 days.

(21) Appl. No.: 15/314,621

(22) PCT Filed: May 28, 2015

(86) PCT No.: PCT/IB2015/054014
§ 371 (c)(1),
(2) Date: Nov. 29, 2016

(87) PCT Pub. No.: WO2015/181767
PCT Pub. Date: Dec. 3, 2015

(65) Prior Publication Data
US 2017/0203112 A1    Jul. 20, 2017

Related U.S. Application Data

(60) Provisional application No. 62/004,872, filed on May 29, 2014.

(51) Int. Cl.
*B65D 69/00*        (2006.01)
*A61B 5/0402*       (2006.01)
(Continued)

(52) U.S. Cl.
CPC ............ *A45C 7/0045* (2013.01); *A61B 5/318* (2021.01); *A61N 1/3625* (2013.01); *A61N 1/3968* (2013.01)

(58) Field of Classification Search
CPC ........ A61N 1/39; A61N 1/3625; A61N 1/375; A61N 1/3968; A45C 7/0045; A61B 5/0402
(Continued)

(56) References Cited

U.S. PATENT DOCUMENTS 3,179,891 A * 4/1965 Sharma ................ G04B 47/006
                                                    206/235
5,314,070 A * 5/1994 Ciarlei ................... G02B 23/26
                                                    206/363
(Continued)

FOREIGN PATENT DOCUMENTS

CN          203169687 U      9/2013
CN          103431771 A     12/2013
(Continued)

*Primary Examiner* — Luan K Bui (57) ABSTRACT

A modular medical device employs a defibrillator/monitor (20) and one or more pouch modules (60). The defibrillator/monitor (20) includes a defibrillator and/or an electrocardiogram ("ECG") monitor (e.g., a defibrillator module and a ECG monitor module). Each pouch module (60) is permanently or detachably adjoined to the defibrillator/monitor (20) and is structurally configured to store one or more accessory items (40, 50) in support of an operation of the defibrillator/monitor (20) (e.g., ECG cable(s), electrode(s), transducer(s), pad(s), data storage device(s), paper, communication device(s), first aid product(s)/fluid(s) and medical supply(ies)/tool(s)). Alternatively, a cradle module (70) having a frame may be employed by the modular medical device to adjoin the pouch module(s) (60) to the defibrillator/monitor (20) and may partially, if not entirely, encircle the defibrillator/monitor (20). The pouch module(s) (60) and/or the cradle module (70) may include storage covers to secure the stored accessory item(s) (40, 50) within the pouch module(s) (60).

18 Claims, 8 Drawing Sheets

(51) Int. Cl.
  *A61N 1/39* (2006.01)
  *A45C 7/00* (2006.01)
  *A61N 1/362* (2006.01)
  *A61B 5/318* (2021.01)

(58) Field of Classification Search
  USPC ... 206/305, 320, 363, 370, 438, 37, 38, 576, 206/570, 572; 220/23.2, 23.4; 607/5
  See application file for complete search history.

(56) References Cited

U.S. PATENT DOCUMENTS

| | | | | |
|---|---|---|---|---|
| 5,470,343 | A * | 11/1995 | Fincke | A61N 1/39 439/341 |
| 5,741,305 | A * | 4/1998 | Vincent | A61N 1/39 439/500 |
| 6,422,669 | B1 * | 7/2002 | Salvatori | A61N 1/39 206/320 |
| 7,530,840 | B2 * | 5/2009 | Lund | B65H 75/362 439/501 |
| 8,730,912 | B2 | 5/2014 | Drapkin et al. | |
| 9,259,594 | B2 | 2/2016 | Roach et al. | |
| 2003/0036775 | A1 | 2/2003 | Salvatori et al. | |
| 2003/0141205 | A1 * | 7/2003 | Cabatic | A61B 50/31 206/305 |
| 2004/0031702 | A1 * | 2/2004 | Mangano | A45C 7/0045 206/6.1 |
| 2005/0065558 | A1 * | 3/2005 | Powers | A61N 1/3968 607/5 |
| 2006/0142806 | A1 * | 6/2006 | Katzman | A61N 1/39 607/5 |
| 2011/0005953 | A1 | 1/2011 | Hochhalter et al. | |
| 2011/0054553 | A1 * | 3/2011 | Cordaro | A61N 1/025 206/363 |
| 2014/0055557 | A1 | 2/2014 | Chung | |
| 2015/0249478 | A1 * | 9/2015 | Greiner | H04B 1/3888 455/575.8 |

FOREIGN PATENT DOCUMENTS

| | | |
|---|---|---|
| DE | 102012103029 A1 | 10/2013 |
| FR | 2961704 A1 | 12/2011 |
| JP | 2007319230 A | 12/2007 |
| JP | 2010500144 A | 1/2010 |
| JP | 3160689 U | 7/2010 |

* cited by examiner

PROTECTIVE CRADLE AND MODULAR POUCHES

This application is a national stage application under 35 U.S.C. § 371 of International Application No. PCT/IB2015/054014 filed on May 28, 2015 and published in the English language on Dec. 3, 2015 as International Publication No. WO2015/181767, which claims priority to U.S. Patent Application No. 62/004,872 filed on May 29, 2014, the entire disclosures of which are incorporated herein by reference.

FIELD OF THE INVENTION

The present disclosure relates to modular medical devices, and more particularly to novel and inventive pouch modules for a defibrillator/monitor that can be used to store accessory items for an operation of the defibrillator/monitor (e.g., ECG cables, monitoring electrodes, data storage systems, etc.).

BACKGROUND OF THE INVENTION

Portable defibrillator/monitors are used in hospitals and outside hospitals for emergency medical care. These devices incorporate one or more vital signs monitoring parameters such as, for example, electrocardiogram ("ECG"), pulse oximetry ("SpO2"), non-invasive blood pressure ("NIBP"), exhaled (end tidal) carbon dioxide ("EtCO2"), temperature and invasive blood pressure ("IBP"). These devices further incorporate electrical therapy delivery capabilities such as, for example, a defibrillation shock (e.g., automatic external defibrillation, synchronized cardioversion and transcutaneous pacing).

In a modular version of a portable defibrillator/monitor, all or part of the patient measurement capability is primarily provided by a ECG measurement module that is separable from a shock therapy module that provides high energy therapy delivery. Typically, accessory items needed to support an operation of the portable defibrillator/monitor are stored and transported by separate carriers.

SUMMARY OF THE INVENTION

The present disclosure provides a modular medical device incorporating novel and inventive pouch modules for a defibrillator/monitor that may be used to store one or more accessory items for an operation of the defibrillator/monitor (e.g., ECG cables, monitoring electrodes, data storage systems, etc.).

One form of the inventions of the present disclosure is a modular medical device employing a defibrillator/monitor and a pouch module. The pouch module is adjoined to the defibrillator/monitor, and structurally configured to store the accessory item(s) in support of an operation of the defibrillator/monitor.

A second form of the invention of the present disclosure is a module medical device employing the defibrillator/monitor, a cradle module, and one or more pouch modules. A frame of the cradle module is adjoined to the defibrillator/monitor, and the pouch modules(s) is(are) adjoined to the frame of the cradle module. The pouch modules are structurally configured to store the accessory item(s) in support of an operation of the defibrillator/monitor.

For purposes of the present disclosure, terms of the art including, but not limited to, "defibrillator", "monitor", "electrocardiogram ("ECG")", "accessory item", "pouch", "cradle" and "module" are to be interpreted as understood in the art of the present disclosure and as exemplary described herein.

For purposes of the present disclosure, the term "defibrillator/monitor" broadly encompasses a defibrillator and/or a ECG monitor. Examples of a defibrillator/monitor include, but are not limited to, patient bedside ECG monitors, portable diagnostic ECG monitors, automated external defibrillators and advanced life support defibrillator/monitors.

For purposes of the present disclosure, the term "adjoin" and any tense thereof broadly encompasses any secure type of connection, coupling, attachment, mounting, affixing, etc. of components involving direct physical contact between the components or an adjacent placements of the components.

The foregoing forms and other forms of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

Figure 1:
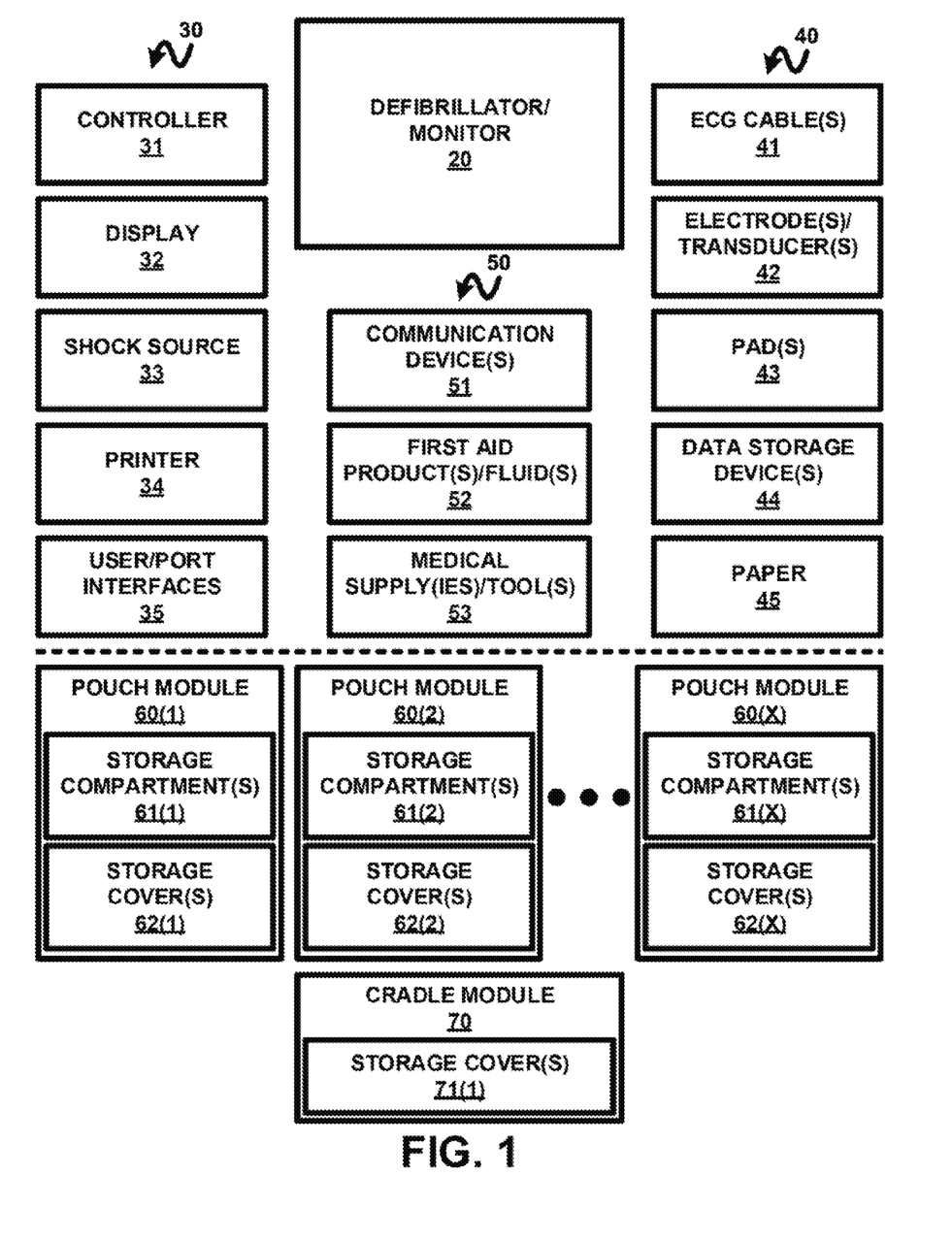
FIG. 1 illustrates a block diagram of various components of modular medical device in accordance with the inventive principles of the present disclosure.

To facilitate an understanding of the present disclosure, the following description of FIG. 1 teaches basic inventive principles of a modular medical device employing an X number of pouch modules, X≥1. From this description, those having ordinary skill in the art will appreciate how to apply the inventive principles of the present disclosure to any type of modular medical device employing X number of pouch modules of identical and/or varying types.

Referring to FIG. 1, the modular medical device employs a defibrillator/monitor 20 incorporating one or more internal components 30 as known in the art including, but not limited to, a controller 31, a display 32, a shock source 33, a printer 34 and user/port interfaces 35. Examples of defibrillator/ monitor 20 include, but are not limited to, patient bedside ECG monitors, portable diagnostic ECG monitors, automated external defibrillators and advanced life support defibrillator/monitors.

Various accessory items 40 and 50 as known in the art are provided to support an operation of defibrillation/monitor 20 (e.g., vital sign monitoring, a defibrillation shock delivery, synchronized cardioversion and transcutaneous pacing). Accessory items 40 facilitate an operation of defibrillation/ monitor 20 and include, but are not limited to, ECG cable(s) 41, electrode(s)/transducer(s) 42, pad(s) 43, data storage device(s) 44 (e.g., USB, SD and flash drives), and paper 45 for printer 34. Accessory items 50 provide additional support for the end user and/or patient in the operation of defibrillation/monitor 20 and include, but are not limited to, communication device(s) 51 (e.g., a mobile phone), first aid product(s)/fluid(s) 52 and medical supply(ies)/tool(s) 53.

Pouch modules 60 are structurally configured to be permanently or detachably adjoined to defibrillator/monitor 20 for storage of one or more accessory items 40 and 50.

In practice, an adjoining of a pouch module 60 to defibrillator/monitor 20 includes, but is not limited to, any secure type of connection, coupling, attachment, mounting, affixing, etc. of the pouch module 60 to/onto defibrillator/ monitor 20 involving direct physical contact between defibrillator/monitor 20 and the pouch module 60, or an adjacent placement of the pouch module 60 to defibrillator/monitor 20. Further, the pouch module 60 may be further structurally configured to be disconnected, uncoupled, detached, removed, dismounted, etc., from defibrillator/monitor 20 for any reason including, but not limited to, a connection, coupling, attachment, mounting, affixing, etc. of the pouch module 60 to another defibrillator/monitor 20. As such, pouch modules 60 as being adjoined to various defibrillator/ modules 20 may be interchangeable and versatile, particularly for both in-hospital use and out-of-hospital emergency care use.

Also in practice, pouch modules 60 may have any configuration, dimensions and material composition (e.g., plastic, rubber, etc.) suitable for being adjoined to a particular type of defibrillator/monitor 20 and for the storage of general or specific types of one or more accessory items (e.g., items 40 and 50) as one having ordinary skill in the art shall appreciate in view of the inventive principles taught herein. In one embodiment as shown, each pouch module 60 includes one or more storage component(s) 61 for storing accessory item(s) and one or more storage covers 62 for securing accessory items(s) stored within storage compartment(s) 61.

Figure 2A:
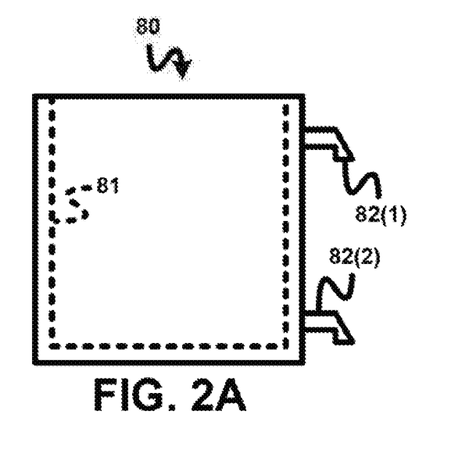
FIGS. 2A-2D illustrates side views of exemplary embodiments of a pouch module in accordance with the inventive principles of the present disclosure.

For example, as shown in FIG. 2A, a general pouch module 80 includes a single storage compartment 81 for storage of accessory item(s) and prongs 82 for attachment to defibrillator/monitor 20.

Figure 2B:
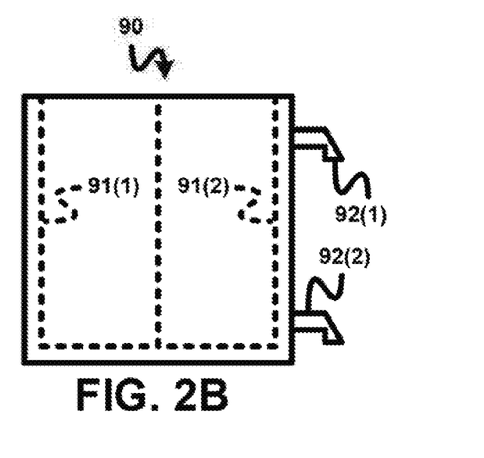

By further example, as shown in FIG. 2B, a general pouch module 90 includes two (2) storage components 91 for storage of accessory item(s) and prongs 92 for attachment to defibrillator/monitor 20.

Figure 2C:
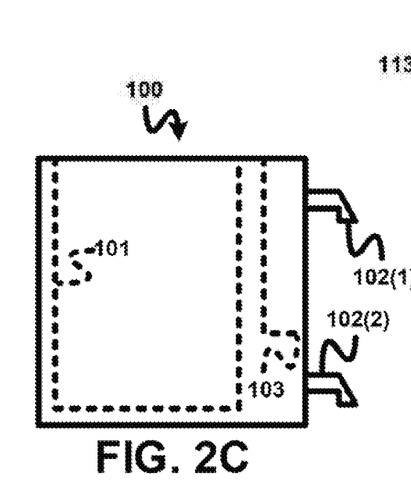

As shown in FIG. 2C, an exemplary printer pouch module 100 includes a storage compartment 101 for storage of accessory item(s) and prongs 102 for attachment to defibrillator. Printer pouch module 100 further includes a paper guide 103 structured and/or configured to guide paper 45 (FIG. 1) during a printing by printer 34 (FIG. 1) to thereby prevent (or greatly minimize the likelihood) of printer paper jamming as subsequently further explained herein in connection with the description of FIGS. 4A-4C.

Figure 2D:
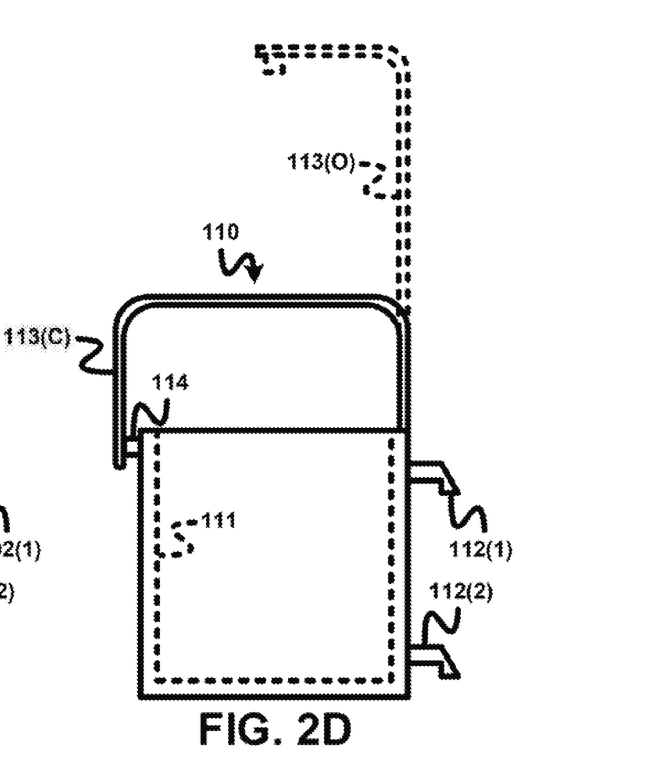

As shown in FIG. 2D, an exemplary covered pouch module 110 includes a storage compartment 111 for storage of accessory item(s) and prongs 112 for attachment to defibrillator. Covered pouch module 110 further includes a storage cover 113 provided/disposed on/for storage component 111 and structured and/or configured to fold over from an open position (O) to a closed position (C) to thereby secure, e.g., via a snap 114 on storage component 111 and storage cover 113, the accessory item(s) stored within storage component 111. In practice, multiple snaps 114 may be used for storage cover 113 to provide added support/security in keeping the storage cover 113 closed and/or spaced so as different snaps or sets of snaps can be used to vary the interior volume of pouch compartment 111, which allows for greater versatility in the number and types and/or sizes of items securely stored therein.

Referring back to FIG. 2C, a storage cover may be attached/disposed on the pouch compartment 101 and/or directly to paper guide 103, and structured and/or configured to fold over and secure, e.g., via a snap on pouch compartment 101 and the storage cover, to hold the paper in place within pouch compartment 101 and to prevent paper and related paper and/or printer items/components in pouch compartment 101 from falling out during transportation.

Figure 3A:
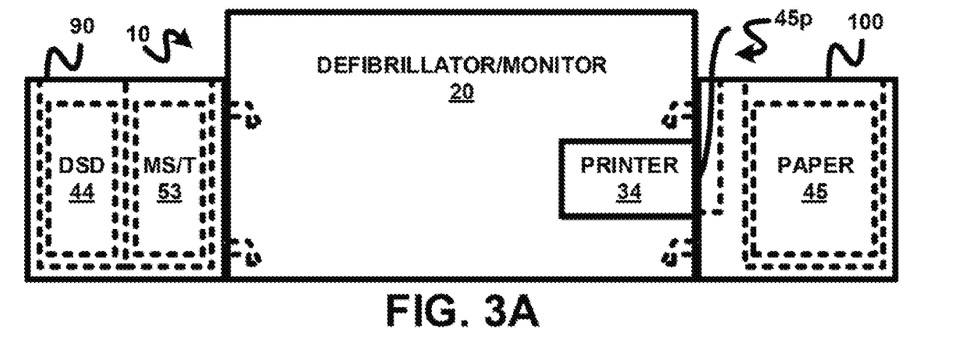
FIGS. 3A-3C illustrates a front view, a top view and a rear view, respectively, of a first exemplary embodiment of a modular medical device in accordance with the inventive principles of the present disclosure.
Figure 3B:
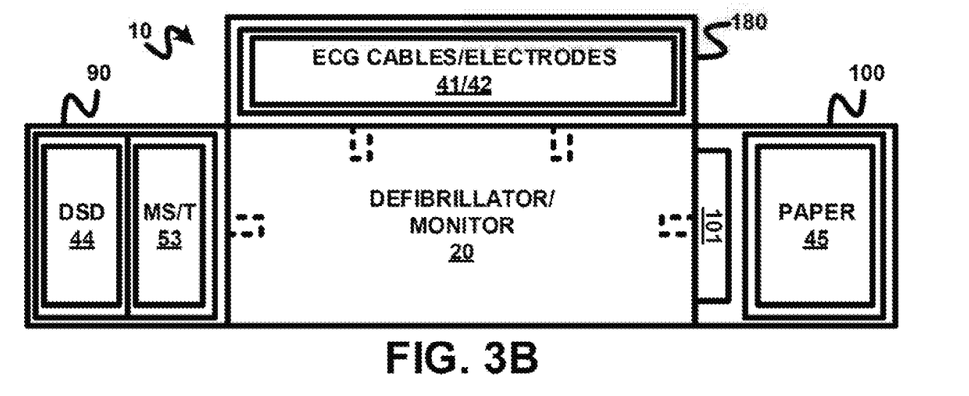
Figure 3C:
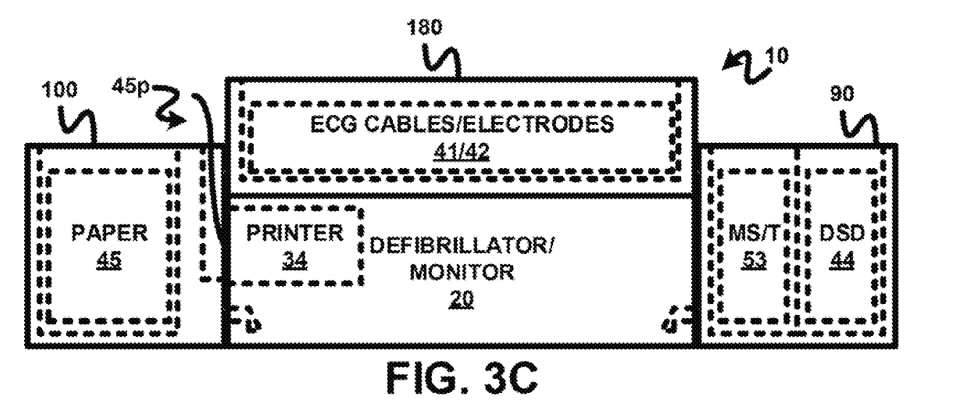

FIGS. 3A-3C illustrates a front view, a top view and a rear view, respectively, modular medical device employing defibrillator/monitor 20, pouch module 90 (FIG. 2B), printer pouch module 100 (FIG. 2C) and a rear pouch module 180. Each pouch module is firmly or detachably adjoined to defibrillator/monitor 20. Pouch module 90 is shown storing a data storage device 44 and medical supplies/tools 53 therein. Printer pouch module 100 is shown storing paper 45 and guiding paper 45P via paper guide 101 during a print operation of printer 34 of defibrillator/monitor 20. A storage cover (not shown) may be included with printer pouch module 100 to provide further guidance of paper 45P. Pouch module 180 is shown storing ECG cables 41 and electrodes 42.

Referring back to FIG. 1, a cradle module 70 is structurally configured to be adjoined to defibrillator/monitor 20 whereby pouch modules 60 permanently (e.g., integrated or detachbly adjoined to cradle module 70.

In practice, an adjoining of cradle module 70 to defibrillator/monitor 20 includes, but is not limited to, any secure type of connection, coupling, attachment, mounting, affixing, etc. of cradle module 70 to/onto defibrillator/monitor 20 involving direct physical contact between cradle module 70 and defibrillator/monitor 20, or an adjacent placement of the pouch module 60 to cradle module 70.

Further, cradle module 70 may be further structurally configured to be disconnected, uncoupled, detached, removed, dismounted, etc., from defibrillator/monitor 20 for any reason including, but not limited to, a connection, coupling, attachment, mounting, etc. of cradle module 70 to another defibrillator/monitor 20. As such, cradle module 70 as adjoinable to may be interchangeable and versatile, particularly for both in-hospital use and out-of-hospital emergency care use.

Also in practice, an adjoining of a pouch module 60 to cradle module 70 includes, but is not limited to, any secure type of connection, coupling, attachment, mounting, affixing, etc. of the pouch module 60 to/onto cradle module 70 involving direct physical contact between the pouch module 60 and cradle module 70, or an adjacent placement of the pouch module 60 to cradle module 70.

Further, the pouch module 60 may be further structurally configured to be disconnected, uncoupled, detached, removed, dismounted, etc., from cradle module 70 for any reason including, but not limited to, a connection, coupling, attachment, mounting, etc. of the pouch module 60 to another cradle module 70. As such, pouch modules 60 as adjoinable to various cradle modules 70 may be interchangeable and versatile, particularly for both in-hospital use and out-of-hospital emergency care use.

Also in practice, cradle module 70 may have any configuration, dimensions and material composition (e.g., plastic, rubber, etc.) suitable for being adjoined to a particular type of defibrillator/monitor 20 and pouch module(s) 60 as one having ordinary skill in the art shall appreciate in view of the inventive principles taught herein. In one embodiment, cradle module 70 partially, if not entirely, encircles defibrillator/monitor 20, and may include one or more storage covers 71 for securing accessory items(s) within storage compartment(s) 61 of pouch module(s) 60.

Figure 4A:
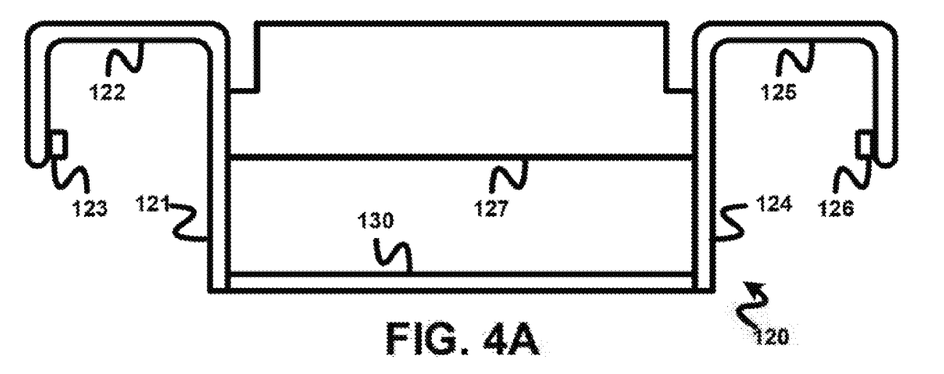
FIGS. 4A-4C illustrates a front view, a side view and a rear view, respectively, of a first exemplary embodiment of a cradle module in accordance with the inventive principles of the present disclosure.
Figure 4B:
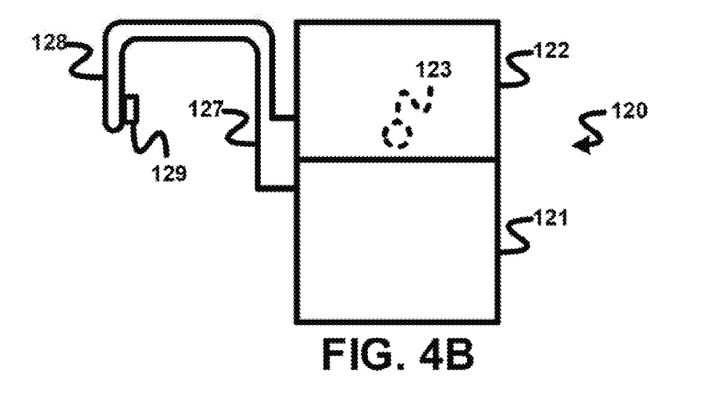
Figure 4C:
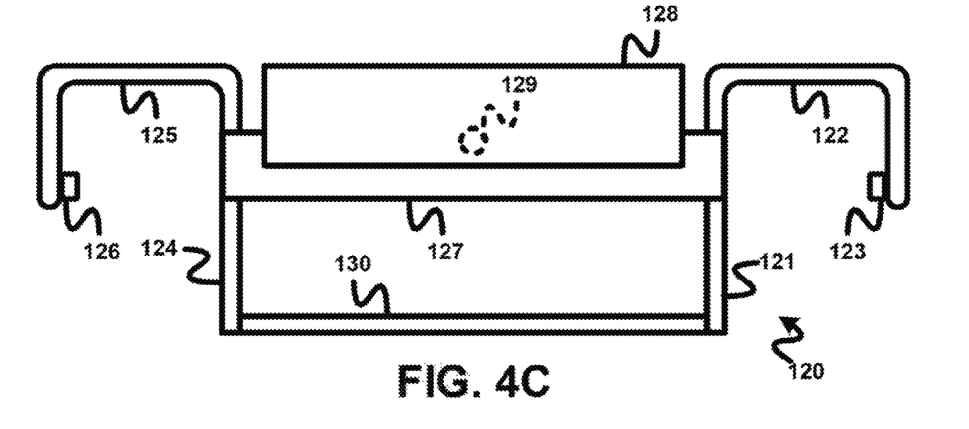

For example, FIGS. 4A-4C illustrates a front view, a top view and a rear view, respectively, a cradle module 120 having a frame with side walls 121 and 124 with a rear wall 127 and a bottom floor 130 integrated therebetween. The frame partially encircles the sides and rear of a defibrillator/monitor. A storage cover 122 upwardly extends from side wall 121, and is structured and/or configured to fold over and secure, e.g., via a snap 123, a pouch module. A storage cover 125 upwardly extends from side wall 124, and is structured and/or configured to fold over and secure, e.g., via a snap 126, a pouch module (not shown). A storage cover 128 upwardly extends from rear wall 127, and is structured and/or configured to fold over and secure, e.g., via a snap 129, a pouch module (not shown).

In practice, walls 121, 124 and 127 and bottom floor 130 may be structurally configured and have material composition to withstand forces applied to the modular medical device, such as, for example, a forcefully placement of the modular medical device of the ground, operating table or any surface for placing the module medical device during an operation of defibrillator/monitor 20. For example, bottom floor 130 may incorporate a rubber/air compressed reinforcement and/or a rubber supports.

Figure 5A:
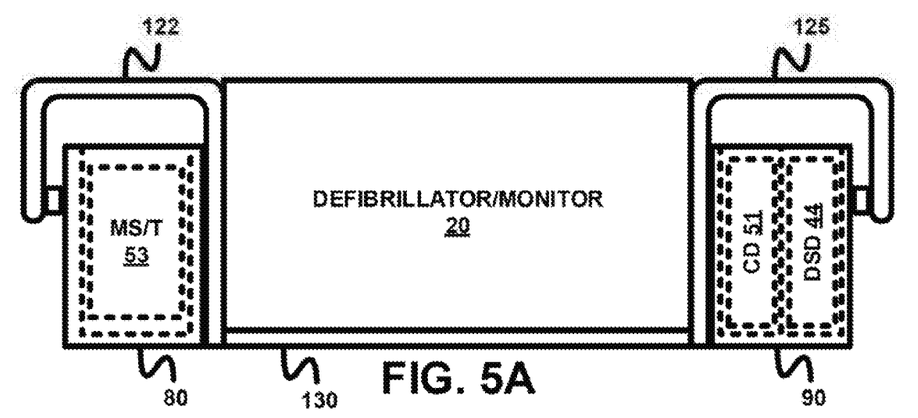
FIGS. 5A-5C illustrates a front view, a side view and a rear view, respectively, of a second exemplary embodiment of a modular medical device in accordance with the inventive principles of the present disclosure.
Figure 5B:
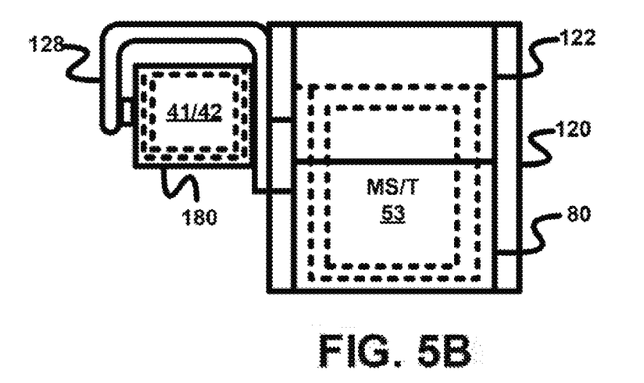
Figure 5C:
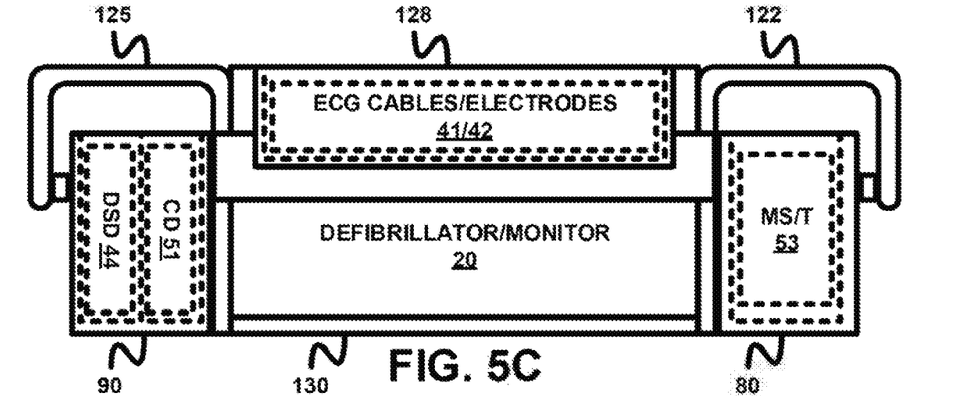

By further example, FIGS. 5A-5C illustrates a front view, a top view and a rear view, respectively, cradle module 120 partially encircling defibrillator/monitor 20 with the walls and floor of cradle module 120 adjoined to the side, rear and bottom of defibrillator/monitor 20. Storage cover 122 is folded over and secured via the snap to pouch module 80 storing medical supply(ies)/tools 53. Storage cover 125 is folded over and secured via the snap to pouch module 90 storing communication device 51 and data storage device 44. Storage cover 128 is folded over and secured via the snap to pouch module 180 storing ECG cable(s)/electrode(s) 41/42. Each pouch module is adjoined to the walls of cradle module 120 whereby the storage covers may be opened to provide access to accessory item(s) with the pouch modules.

Figure 6:
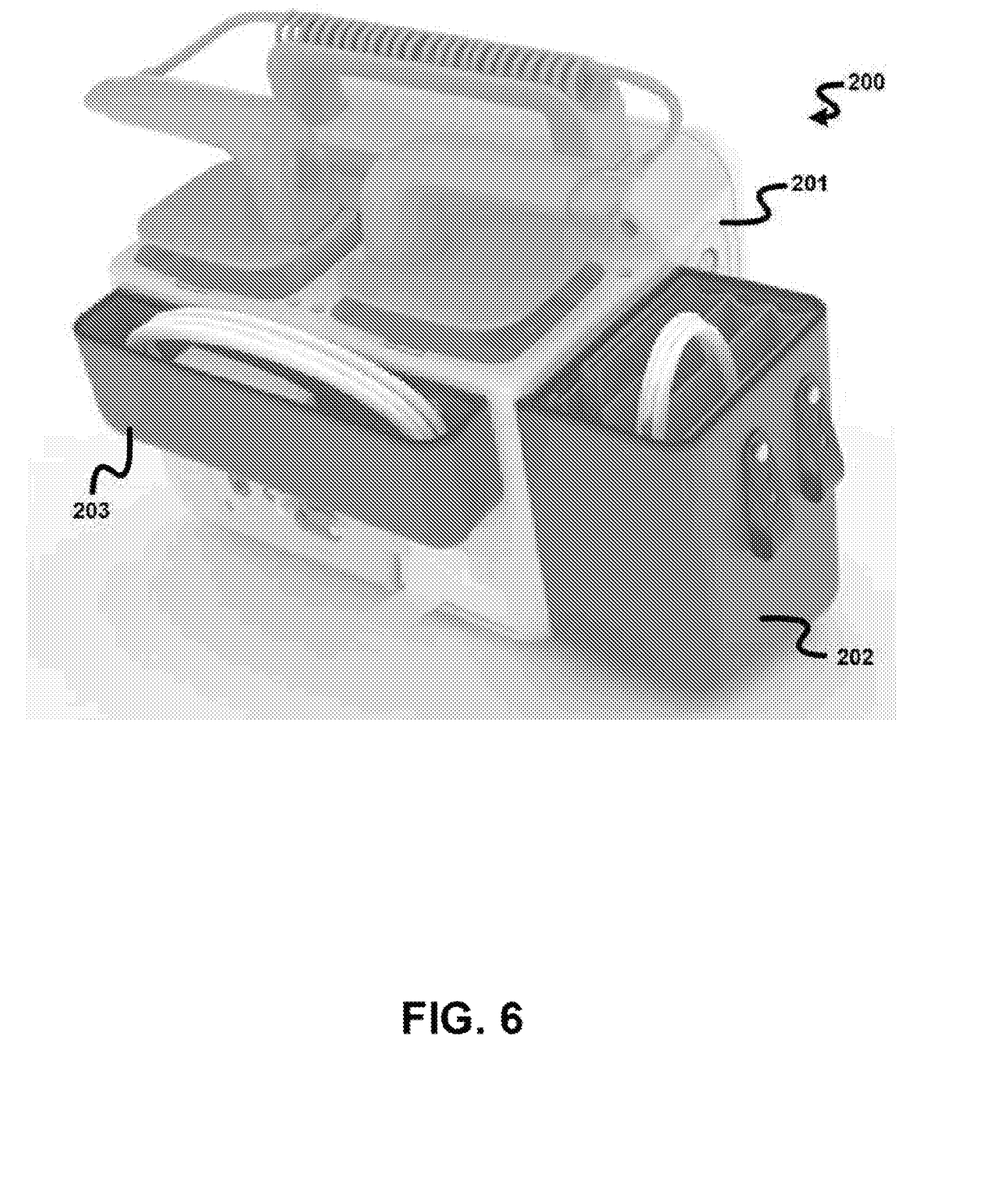
FIG. 6 illustrates a perspective view of an exemplary coupling of in-hospital modular medical device in accordance with the inventive principles of the present disclosure.
Figure 7:
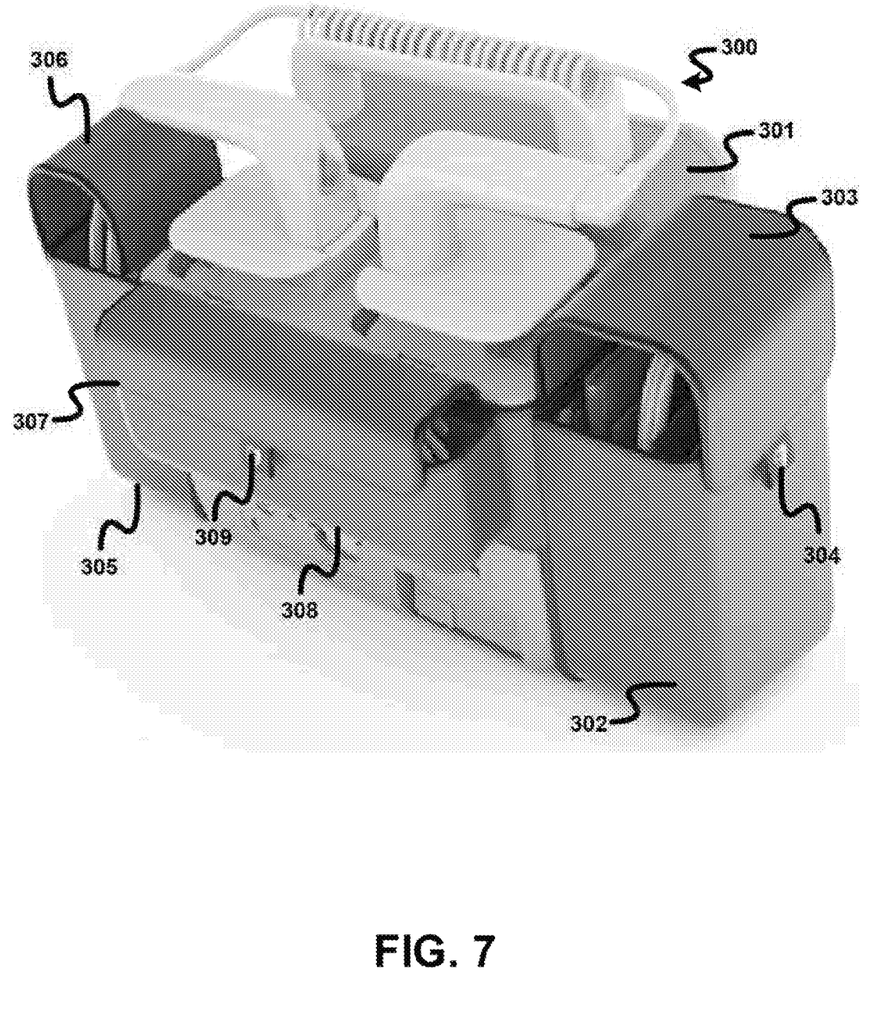
FIG. 7 illustrates a perspective view of an exemplary coupling of out-of-hospital modular medical device in accordance with the inventive principles of the present disclosure.

To provide a more visual example, in accordance with the teachings herein, FIG. 6 illustrates an modular medical device 200 employing an in-hospital defibrillator/monitor 201 and pouch modules 202 and 203, and FIG. 7 illustrates an modular medical device 300 employing an out-of-hospital defibrillator/monitor 301, and a cradle module having a storage cover 303 folded over and secured via a snap 304 to a side connector pouch module 302, a storage cover 306 folded over and secured via a snap (not shown) to a printer pouch module 305, and a storage cover 307 folded over and secured via a snap 309 to a rear connector pouch module 308.

Of importance to note is the versatility of pouch modules and the cradle module of the present disclosure. For example, a modular medical device based on the modular medical device shown in FIG. 6 may employ (1) a side connector pouch module, (2) a rear connector pouch module, (3) a printer connector pouch module, (4) a side connector pouch module and a rear connector pouch module, (5) a side connector pouch module and a printer pouch module, (6) a rear connector module and a printer pouch module or (7) both connector modules and the printer module.

By further example, a modular medical device based on the modular medical device shown in FIG. 7 may employ a cradle with one of the aforementioned seven (7) combinations of side connector pouch module, rear connector pouch module and printer pouch module.

Figure 8A:
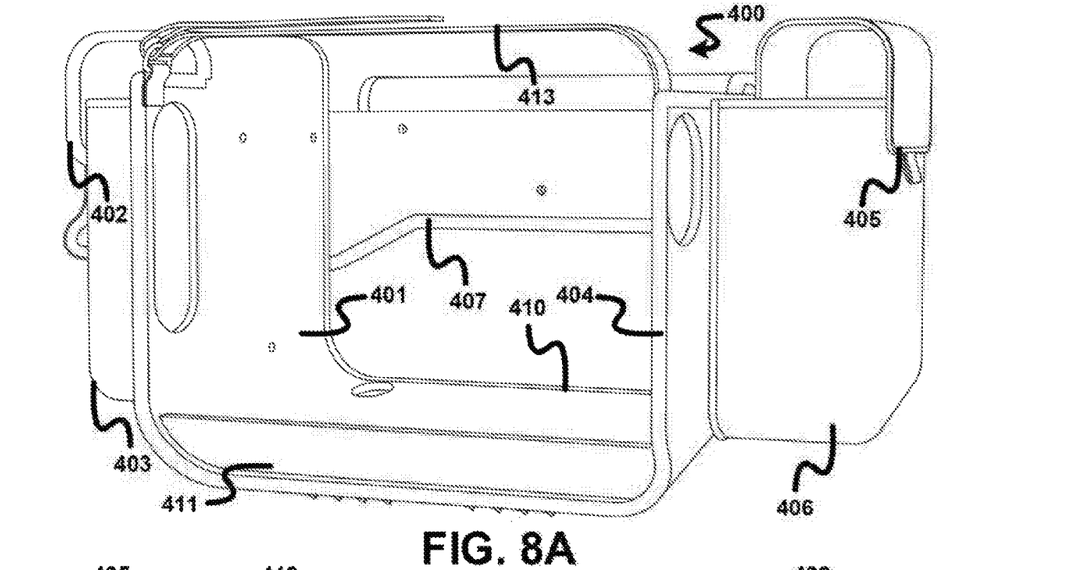
FIGS. 8A and 8B illustrate a front perspective view and a rear perspective view, respectively, of a second exemplary embodiment of a cradle module in accordance with the inventive principles of the present disclosure.
Figure 8B:
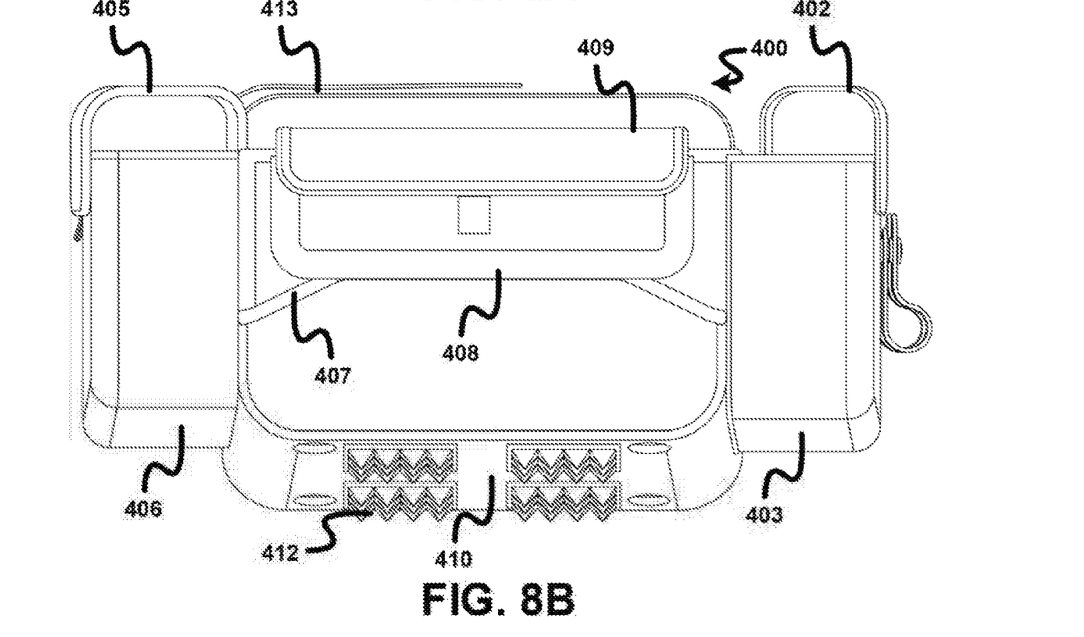

Additionally, FIGS. 8A and 8B illustrates a front perspective and a rear perspective view, respectively, a cradle module 400 having a frame with side walls 401 and 404 with a rear wall 407 and a bottom floor 410 integrated therebetween. The frame is structurally configure to partially encircle the sides, rear and bottom of a defibrillator/monitor. A storage cover 402 upwardly extends from side wall 401, and is structured and/or configured to fold over and secure, e.g., via a snap, a pouch module 403. A storage cover 405 upwardly extends from side wall 404, and is structured and/or configured to fold over and secure, e.g., via a snap, a pouch module 406. A storage cover 408 upwardly extends from rear wall 407, and is structured and/or configured to fold over and secure, e.g., via a snap, a pouch module 409. Bottom floor 410 incorporate reinforced rubber 411 and rubber stops 412. Also included is a securing strap 413 coupled to sides walls 401 and 404 whereby securing strap 413 is used to secure a defibrillator/monitor seated within the frame.

While this invention has been described with respect to defibrillators/monitors as illustrated, such as an in-hospital defibrillator/monitor (e.g., used by hospital personnel) and an out-of-hospital defibrillator/monitor (e.g., used by EMS personnel), one having ordinary skill in the art shall appreciate in view of the teaching provided herein that exemplary embodiments of the present disclosure can be implemented in other medical devices, including, but not limited to, patient monitors (e.g., ECG monitors), automatic external defibrillators (AEDs) and/or other defibrillators. Indeed, exemplary embodiments of the present disclosure implemented in these other types of products are specifically contemplated and considered to be within the scope of the present disclosure.

Referring to FIGS. 1-8, those having ordinary skill in the art will appreciate numerous benefits of the present disclosure including, but not limited to, a defibrillator/monitor providing flexibility to an end user for storing accessory items, particularly resuscitation related items.

Further, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components embodying the principles of the invention.

Having described preferred and exemplary embodiments of the present disclosure, which embodiments are intended to be illustrative and not limiting, it is noted that modifications and variations can be made by persons skilled in the art in light of the teachings provided herein, including the Figures. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device/system or such as may be used/implemented in/with a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. A modular medical device, comprising:
a defibrillator/monitor including at least one of a defibrillator or an ECG monitor; and
a pouch module,
  wherein the pouch module includes at least one storage compartment having an access opening to store at least one accessory item in support of an operation of the defibrillator/monitor,
  wherein the pouch module further includes a storage cover operable to be transitioned between an open position and a closed position relative to the access opening of the at least one storage compartment,
  wherein the pouch module is directly adjoinable to the defibrillator/monitor by a connectable and disconnectable connection, and
  wherein the at least one accessory item as stored in the pouch module is accessible through the access opening when the pouch module is adjoined to the defibrillator/monitor and when the storage cover is in the closed position.

2. The modular medical device of claim 1, wherein the storage cover is structurally configured to spatially fold over the access opening of the pouch module when the storage cover is in the closed position.

3. The modular medical device of claim 1,
wherein the defibrillator/monitor includes a printer; and
wherein the pouch module is structurally configured to guide paper in support of a print operation of the printer.

4. The modular medical device of claim 1,
wherein the storage cover has a releasable connection to the at least one storage compartment; and
wherein the storage cover being releasable connected to the at least one storage compartment defines the closed position.

5. The modular medical device of claim 1,
wherein the storage cover has a plurality of releasable connections to the at least one storage compartment; and
wherein the storage cover being releasable connected to the at least one storage compartment defines one of a plurality of closed positions including the closed position.

6. A modular medical device, comprising:
a defibrillator/monitor including at least one of a defibrillator or an ECG monitor;
a cradle module including a frame adjoinable to the defibrillator/monitor by a connectable and disconnectable connection;
a pouch module permanently adjoined to the frame of the cradle module,
  wherein the pouch module includes at least one storage compartment having an access opening to store at least one accessory item in support of an operation of the defibrillator/monitor; and
a storage cover operable to be transitioned between an open position and a closed position relative to the access opening of the at least one storage compartment,
  wherein the at least one accessary item as stored in the pouch module is accessible through the access opening when the frame is adjoined to the defibrillator/monitor and when the storage cover is in the closed position.

7. The modular medical device of claim 6, wherein the storage cover is structurally configured to spatially fold over the access opening of the pouch module when the storage cover is in the closed position.

8. The modular medical device of claim 6, wherein the pouch module includes the storage cover structurally configured to spatially fold over the access opening of the pouch module when the storage cover is in the closed position.

9. The modular medical device of claim 6, wherein the cradle module includes the storage cover structurally configured to spatially fold over the access opening of the pouch module when the storage cover is in the closed position.

10. The modular medical device of claim 6,
wherein the defibrillator/monitor includes a printer; and
wherein the pouch module is structurally configured to guide paper in support of a print operation of the printer.

11. The modular medical device of claim 6, wherein the frame of the cradle module is structurally configured to at least partially encircle the defibrillator/monitor.

12. The modular medical device of claim 6, wherein the frame includes side walls and one or more of a rear wall or a bottom floor integrated between the side walls.

13. The modular medical device of claim 12, wherein the bottom floor includes at least one of a rubber reinforcement or an air compressed reinforcement.

14. The modular medical device of claim 12, wherein the bottom floor includes at least one rubber stop.

15. The modular medical device of claim 8, wherein the storage cover has a releasable connection to the at least one storage compartment.

16. The modular medical device of claim 6, wherein the frame includes side walls and a securing strap for coupling the side walls.

17. The modular medical device of claim 6, wherein the storage cover has a releasable connection to the at least one storage compartment; and
wherein the storage cover being releasable connected to the at least one storage compartment defines the closed position.

18. The modular medical device of claim 6,
wherein the storage cover has a plurality of releasable connections to the at least one storage compartment; and
wherein the storage cover being releasable connected to the at least one storage compartment defines one of a plurality of closed positions including the closed position.

* * * * *